United States Patent
Hepbildikler et al.

(10) Patent No.: US 8,822,655 B2
(45) Date of Patent: Sep. 2, 2014

(54) PRE-FILTRATION ADJUSTMENT OF BUFFER SOLUTES

(75) Inventors: Stefan Hepbildikler, Munich (DE); Wolfgang Kuhne, Penzberg (DE); Eva Rosenberg, Munich (DE); Gerhard Winter, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 355 days.

(21) Appl. No.: 13/395,893

(22) PCT Filed: Aug. 27, 2010

(86) PCT No.: PCT/EP2010/062554
§ 371 (c)(1), (2), (4) Date: May 16, 2012

(87) PCT Pub. No.: WO2011/039012
PCT Pub. Date: Apr. 7, 2011

(65) Prior Publication Data
US 2012/0219990 A1 Aug. 30, 2012

(30) Foreign Application Priority Data

Sep. 29, 2009 (EP) ..................................... 09012316

(51) Int. Cl.
| | | |
|---|---|---|
| C07K 16/00 | (2006.01) | |
| A23J 1/00 | (2006.01) | |
| C07K 1/14 | (2006.01) | |
| C07K 1/34 | (2006.01) | |
| B01D 61/00 | (2006.01) | |
| B01D 61/14 | (2006.01) | |
| C07K 16/18 | (2006.01) | |

(52) U.S. Cl.
CPC ... *C07K 1/14* (2013.01); *C07K 1/34* (2013.01); *B01D 61/00* (2013.01); *B01D 61/14* (2013.01); *C07K 16/18* (2013.01)
USPC .......................... 530/412; 530/387.1; 530/414

(58) Field of Classification Search
None
See application file for complete search history.

(56) References Cited

U.S. PATENT DOCUMENTS

| | | |
|---|---|---|
| 5,490,937 A | 2/1996 | van Reis |
| 2005/0169925 A1 | 8/2005 | Bardroff et al. |
| 2005/0226876 A1 | 10/2005 | Graus et al. |

FOREIGN PATENT DOCUMENTS

| | | |
|---|---|---|
| WO | 03/070760 | 8/2003 |
| WO | 2005/100402 | 10/2005 |
| WO | 2006/031560 | 3/2006 |
| WO | 2009/010269 | 1/2009 |

OTHER PUBLICATIONS

Faude, A. et al., Journal of Chromatography 1161:29-35 ( 2007).
Winzor, D et al., Anal. Biochem. 333:225-229 ( 2004).
Daugherty, A. et al., Advanced Drgu jDelivery Rev 58:686-706 ( 2006).
Saxena, A. et al., Advances in Collid and Interface Science 145:1-22 ( 2009).
Van Reis, et al., Journal of Membrane Science 129:19-29 ( 1997).
Capelle, M et al., Eur. Journal of Pharm. Biopharm 65:131-148 ( 2007).
Nakatsuka, S. et al., Journal of Membrane Science 69( SUPPL 189-211) ( 1992).
Mignard, D et al., Journal of Membrane Science 186:133-143 ( 2001).
(Written Opinion by Internat'l Search Authority in PCT/EP2010/062554 Jul. 29, 2011).
The Japanese Office Action, issued on Jan. 8, 2014, in the corresponding Japanese application No. 2012-530201.

*Primary Examiner* — Daniel E. Kolker
*Assistant Examiner* — James Rogers

(57) ABSTRACT

Herein is reported a tangential flow filtration method with a pre-filtration solute concentration adjustment in order to ensure a defined concentration of the components of the solution after tangential flow filtration.

13 Claims, 10 Drawing Sheets

PRE-FILTRATION ADJUSTMENT OF BUFFER SOLUTES

PRIORITY TO RELATED APPLICATION(S)

This application claims the benefit of European Patent Application No. 09012316.7 filed Sep. 29, 2009 and International Patent Application PCT/EP2010/062554, filed Aug. 27, 2010. The entire contents of the above-identified applications are hereby incorporated by reference.

Herein is reported a method for the pre-filtration adjustment of the solute concentration prior to a tangential flow filtration in order to obtain a bulk pharmaceutical active protein ingredient.

BACKGROUND OF THE INVENTION

Polypeptides play an important role in today's medical portfolio. Expression systems for the production of recombinant polypeptides are well-known. For human application every pharmaceutical substance has to meet distinct criteria. To ensure the safety of biopharmaceutical agents to humans, for example, nucleic acids, viruses, and host cell proteins, which would cause severe harm, have to be removed. To meet the regulatory specification one or more purification steps have to follow the manufacturing process. Among other, purity, throughput, and yield play an important role in determining an appropriate purification process.

Due to their chemical and physical properties, such as molecular weight and domain architecture, including secondary modifications, the downstream processing of immunoglobulins is essential. For example, concentrated solutions are required not only for formulated drugs but also for intermediates in downstream processing (DSP) to achieve low volumes for economic handling and application storage. Furthermore, fast concentration processes are favored to ensure smooth processes and short operating times. In this context tangential flow filtration (TFF) processes are used.

Saxena, A., et al. report membrane-based techniques for the separation and purification of proteins (Adv. Colloid Interfacial Sci. 145 (2009) 1-22. In WO 2009/010269 a variable tangential flow filtration method is reported. Mignard, D., et al. report fouling during the cross-flow ultrafiltration of proteins (J. Membr. Sci. 186 (2001) 133-143). An optimization diagram for membrane separations is reported by Van Reis, R., et al., J. Membr. Sci. 129 (1997) 19-29).

Thermodynamic non-ideality of protein containing solutions during membrane based processes has been reported by Donnan, F. G., Z. Elektrochem. 17 (1911) 572-581. Stoner et al. (J. Pharm. Sci. 93 (2004) 2332-2342) reported the concentration of charged solutes encompassing chloride, histidine and acetate during dialysis of the different proteins at various protein concentrations.

SUMMARY OF THE INVENTION

One aspect as reported herein is an ultrafiltration method for concentrating an immunoglobulin solution comprising the following steps:

a) providing an immunoglobulin solution with a pH value and with a first concentration $S^+$ or $S^-$ of a buffer substance, b) adjusting the first concentration of the buffer substance to a second concentration $S'$ and maintaining the pH value, whereby the second concentration $S'$ is calculated with equation 2 if the buffer substance is a cation/neutral pair or with equation 3 if the buffer substance is a neutral/anion pair, c) concentrating the solution of b) by a tangential flow filtration, wherein equation 2 is $$S^+ = \frac{-zP + \sqrt{(zP)^2 + 4\left(\frac{S'}{\rho'}\left(\rho - \frac{PM_P}{1000}\right)\right)^2}}{2}$$

and equation 3 is $$S^- = \frac{zP + \sqrt{(zP)^2 + 4\left(\frac{S'}{\rho'}\left(\rho - \frac{PM_P}{1000}\right)\right)^2}}{2}$$

with
the molar concentration in the retentate of positively/negatively charged solutes ($S^+/S^-$), the charge of the protein (z), the molar concentration (P) and the molecular weight ($M_p$) of the protein, the density of the solution in the retentate ($\rho$) and the permeate ($\rho'$), and the theoretical molar concentration of the diffusible solute ($S'$), whereby the theoretical diffusible solute concentration $S'$ is corrected by a correction factor that is considering the pH value wherein the ratio between buffer anion/buffer cation and buffer acid is calculated for each pH value determined in the retentate by using the Henderson-Hasselbach-Equation and the relative increase at each pH value is used as the respective correction factor.

In one embodiment the buffer substance is histidine and that the second concentration is calculated with equation 2. In one embodiment the pH value is of from pH 5.0 to pH 6.0. In a further embodiment the pH value is pH 5.5. In another embodiment the first concentration is approximately 20 mM. In a further embodiment the second concentration is of from 24 mM to 37 mM with a protein concentration of the concentrated solution of from 100 g/l to 300 g/l, respectively. In one embodiment the protein concentration is approximately 200 g/l and the second concentration is of from 28 mM to 31 mM. In another embodiment the first concentration is approximately 46 mM. In a further embodiment the second concentration is of from 52 mM to 72 mM with a protein concentration of the concentrated solution of from 100 to 300 g/l, respectively. In one embodiment the protein concentration is approximately 200 g/l and the second concentration is of from 59 mM to 62 mM.

In another embodiment the buffer substance is acetate and the concentration is calculated with equation 3. In one embodiment the pH value is of from pH 4.5 to pH 6.0. In a further embodiment the pH value is pH 5.5. In another embodiment the first concentration is approximately 20 mM. In a further embodiment the second concentration is of from 8 mM to 19 mM with a protein concentration of the concentrated solution of from 300 g/l to 100 g/l, respectively. In one embodiment the protein concentration is approximately 200 g/l and the second concentration is of from 12 mM to 17 mM. In another embodiment the first concentration is approximately 45 mM. In a further embodiment the second concentration is of from 41 mM to 48 mM with a protein concentration of the concentrated solution of from 300 to 100 g/l, respectively. In one embodiment the protein concentration is approximately 200 g/l and the second concentration is of from 43 mM to 47 mM.

In one embodiment the immunoglobulin is an anti-P-selectin antibody or an anti-Aβ antibody.

Another aspect as reported herein is a method for producing an immunoglobulin in vitro comprising
a) cultivating a cell comprising a nucleic acid encoding the immunoglobulin,
b) recovering the immunoglobulin from the cultivation medium or the cell of step a)
c) purifying the immunoglobulin,
d) concentrating the immunoglobulin with a method as reported herein and thereby producing an immunoglobulin.

DETAILED DESCRIPTION OF THE INVENTION

Herein is reported a tangential flow filtration method with a pre-filtration solute concentration adjustment in order to ensure a defined concentration of the components of the solution after tangential flow filtration.

The term "cation/neutral pair" denotes a buffer substance which provides for a buffer system consisting of the buffer substance in neutral form and the buffer substance in protonated, i.e. positively charge form, as cation. One example thereof is histidine. The term "neutral/anion pair" denotes a buffer substance which provides for a buffer system consisting of the buffer substance in neutral form and the buffer substance in de-protonated, i.e. negatively charge form, as anion. One example is acetate.

The term "tangential flow filtration", or short "TFF", denotes a filtration process wherein a solution containing a polypeptide to be concentrated flows along, i.e. tangential, to the surface of a filtration membrane. The filtration membrane has a pore size with a certain cut off value. In one embodiment the cut off value is in the range of 20 kDa to 50 kDa, in another embodiment of 30 kDa. TFF was conducted as ultra filtration. The term "cross-flow" denotes the flow of the solution to be concentrated tangential to the membrane (retentate flow). The term "flux" or "permeate flow", which can be used interchangeably, denotes the flow of fluid through the membrane, i.e. through the pores of the membrane. That is, it denotes the volumetric rate of the permeate flow through the membrane. A flow is usually given in terms of volume per unit membrane area per unit time as liters/m²/h (LMH). The permeate comprises the solvent of the solution to be concentrated on the retentate side as well as molecules with a molecular weight below the cut off value of the employed membrane but not the polypeptide to be concentrated. The terms "transmembrane pressure" or "TMP", which can be used interchangeably, denote the pressure which is applied to drive the solvent and components smaller than the cut off value of the membrane through the pores of the membrane. The transmembrane pressure is an average pressure of the inlet, outlet and permeate and can be calculated as:

$$TMP = \frac{(p_{in} + p_{out})}{2} - p_{permeate}. \qquad \text{(equation 1)}$$

The term "solute" as used herein denotes all components, i.e. ionic and non-ionic, of a solution to be concentrated except the water molecules and the molecules of the polypeptide to be concentrated. Generally comprises the solution to be concentrated a polypeptide, water and a buffer salt, and optionally a non-buffer salt, such as sodium chloride.

A "polypeptide" is a polymer of amino acid residues joined by peptide bonds, whether produced naturally or synthetically. Polypeptides of less than about 20 amino acid residues are referred to as "peptides". A "protein" is a macromolecule comprising one or more polypeptide chains or at least one polypeptide chain of more than 100 amino acid residues. A polypeptide may also comprise non-peptidic components, such as carbohydrate groups. Carbohydrates and other non-peptidic substituents may be added to a polypeptide by the cell in which the polypeptide is produced, and will vary with the type of cell. Polypeptides are defined herein in terms of their amino acid backbone structures; substituents such as carbohydrate groups are generally not specified, but may be present nonetheless.

The term "immunoglobulin" refers to a protein consisting of one or more polypeptide(s) substantially encoded by immunoglobulin genes. The recognized immunoglobulin genes include the different constant region genes as well as the myriad immunoglobulin variable region genes. Immunoglobulins may exist in a variety of formats, including, for example, Fv, Fab, and F(ab)$_2$ as well as single chains (scFv) or diabodies (in general, Hood, L. E., et al., Immunology, The Benjamin N.Y., $2^{nd}$ edition (1984)). The term "immunoglobulin", thus, denotes a complete immunoglobulin consisting of two immunoglobulin heavy chains and two immunoglobulin light chains, as well as an "immunoglobulin fragment" comprising at least one domain selected from the variable domain, the $C_H1$ domain, the hinge-region, the $C_H2$ domain, the $C_H3$ domain, or the $C_H4$ domain of a heavy chain, or the variable domain or the $C_L$ domain of a light chain and an "immunoglobulin conjugate" comprising at least one domain of an immunoglobulin heavy or light chain conjugated via a peptide bond to a further polypeptide. The further polypeptide is a non-immunoglobulin peptide, such as a hormone, or toxin, or growth receptor, or antifusogenic peptide, or complement factor, or the like.

For the purification of biotechnologically produced immunoglobulins often a combination of different column chromatography steps is employed. In one embodiment a protein A affinity chromatography is followed by one or two additional separation steps. The final purification step is a so called "polishing step" for the removal of trace impurities and contaminants like aggregated immunoglobulins, residual HCP (host cell protein), DNA (host cell nucleic acid), viruses, or endotoxins. For this polishing step in one embodiment an anion exchange material in a flow-through mode is used.

Different methods are well established and widespread used for protein recovery and purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis). These methods can be combined independently in different embodiments of the current invention.

The term "immunoglobulin in monomeric form" and grammatical equivalents thereof denotes an immunoglobulin molecule not associated with a second immunoglobulin molecule, i.e. neither covalently nor non-covalently bound to another immunoglobulin molecule. The term "immunoglobulin in aggregated form" and grammatical equivalents thereof denotes an immunoglobulin molecule which is associated, either covalently or non-covalently, with at least one additional immunoglobulin molecule or fragment thereof, and which is eluted in a single peak from a size exclusion chromatography column. The term "in monomeric form" and grammatical equivalents thereof as used within this application not necessarily denotes that 100% of an immunoglobulin molecule are present in monomeric form. It denotes that an immunoglobulin is essentially in monomeric form, i.e. at least 90% of the immunoglobulin is in monomeric from, in one embodiment at least 95% of the immunoglobulin is in monomeric form, in another embodiment at least 98% of the immunoglobulin is in monomeric form, in a further embodiment at least 99% of the immunoglobulin is in monomeric form, and in a final embodiment more than 99% of the immunoglobulin is in monomeric form determined as peak area of a size exclusion chromatogram of the immunoglobulin preparation. The term "in monomeric and in aggregated form" denotes a mixture of immunoglobulin molecules not associated with other immunoglobulin molecules and of immunoglobulin molecules associated with other immunoglobulin molecules. In this mixture neither of the monomeric form nor the aggregated form is present exclusively. The term "high molecular weight (HMW) form" denotes polymeric, i.e. aggregated, immunoglobulin, whereby the aggregate is still soluble in an aqueous buffered solution.

The term "100%" as used within this application denotes that the amount of components other than a specified component are below the detection limit of the referred to analytical method under the specified conditions.

The terms "90%", "95%", "98%", "99%" as used within this application denote no exact values but values within the accuracy of the referred to analytical method under the specified conditions.

Generally ion exchange chromatography in flow-through mode is the final chromatographic step in purification processes of monoclonal immunoglobulins to remove residual host cell DNA, endotoxins and retrovirus-like particles. Hence, the purified ion exchange chromatography pool is in e.g. a phosphate- or tris (hydroxymethyl)-aminomethan buffer. Subsequently, the conditions have to be changed to a buffer system for e.g. ensuring stability of the active pharmaceutical ingredient during storage. Generally the pH value is slightly acidic e.g. between pH 5 and pH 6 and a conductivity of less than 5 mS/cm is required (Daugherty, A. L. and Mrsny, R. J., Adv. Drug Deliv. Rev. 58 (2006) 686-706).

Concomitantly the ion exchange pool is the basis buffer for formulation by using/adding different stock solutions of excipients like surfactants and sugars. Therefore, the ion exchange chromatography pool is concentrated and diafiltered into a suitable buffer composition by ultrafiltration to provide a defined composition of protein, buffer solutes, pH and conductivity.

Electrostatic interactions of ions and polypeptides at non-isoelectric pH values lead to unequal partitioning thereof during an ultrafiltration process on the retentate and permeate side of the ultrafiltration membrane. This results in a significant variation of solute concentration before and after tangential flow filtration (for concentration and diafiltration) and results in variations in pH and conductivity before, during and after the tangential flow filtration.

For example, an immunoglobulin ion exchange chromatography pool was diafiltered against 20 mM histidine buffer (pH 5.5; 1.6 mS/cm) of a 1 to 10-fold diafiltration volume (DV) with respect to the pool volume. Thereafter, the diafiltered pool was concentrated to more than 210 mg/ml protein concentration in a tangential flow filtration. It has been found that even after applying a 10-fold diafiltration volume the predefined conditions for the histidine buffer system concerning pH value and conductivity could not be maintained constant after the complete concentration process. After starting the concentration process the pH value increases to pH 5.7 and conductivity reaches 2.2 mS/cm at a protein concentration of 215 mg/ml in the retentate.

Moreover, conductivity and pH value were monitored during the UF concentration process in 20 mM histidine buffer at pH 5.5. With increased protein concentration an increase in conductivity was observed again. In addition, an increase in the pH value up to pH 5.8 was observed as well.

A different but also similar observation was made during an UF concentration processes with another buffer system (20 mM acetate buffer at pH 5.5). During the UF process the pH value increased to pH 5.8 similar as observed with the 20 mM histidine buffer, but the conductivity decreased with increasing protein concentration. Essentially the same was observed at a higher acetate concentration of 45 mM at pH 5.0.

During the UF concentration process of the monoclonal immunoglobulin in two different, defined buffer systems, a significant accumulation of the buffer substance in the case of acetate in the retentate, and a significant loss of the buffer substance in the case of histidine in the retentate has been observed (see e.g. FIGS. 1 and 3). The concentration of acetate nearly doubled whereas the concentration of histidine was halved at an immunoglobulin concentration of about 200 mg/ml. Both induced changes in conductivity and pH during the concentration process.

The unequal partitioning of the solute compounds during diafiltration and concentration operations results in excipient concentrations, pH and conductivity values which are significantly different from those of the diafiltration buffer at the start of the process. As this can influence stability of the final formulated immunoglobulin the preset solute compound concentration are required to be present in the concentrated immunoglobulin preparation.

Different possibilities to correct the changes during tangential flow filtration are likely:
restock/dilute with buffer solution after concentration,
adjustment of the pH value close to the isoelectric point value before the tangential flow filtration (see e.g. FIG. 2),
defined addition/reduction of solute prior to tangential flow filtration (see e.g. FIG. 4).

The dilution after the UF with buffer solution is not suited as this will result also in a dilution and reduction of the immunoglobulin concentration. This is in direct opposite to the intention of the UF process to provide concentrated immunoglobulin solutions.

It has now been found that the defined addition/reduction of solute concentration prior to the tangential flow filtration process is advantageous in order to correct the concentration changes independent of the concentration device, membrane material, and concentration parameters. It has been found that as in one embodiment in case of a histidine buffer (=solute) an adjustment at about pH 5.0 to 29.6 mM and 60 mM histidine, respectively, before tangential flow filtration is required to achieve a predefined histidine buffer concentration of 20 mM and 46 mM histidine, respectively, after the tangential flow filtration in the concentration of an immunoglobulin of the IgG 1 and IgG 4 class to 215 mg/ml.

In an alternative way of addressing the concentration changes during the ultrafiltration process the concentrates were readjusted to a pH value of pH 5.0 by adding 0.5 M hydrochloric acid (HCl) to the stirred solution after the UF process. This was only necessary for the solutions which were concentrated at pH 7.5 and at 20 mM histidine pH 5.0 due to the pH shift during UF. The experiments conducted at 29.6 mM histidine pH 5.0 did not show a pH shift as reported before. Table 1 shows the pH values before UF, after UF and after readjustment to pH 5.0.

TABLE 1

| starting conditions | pH before UF | pH after UF | pH end product |
|---|---|---|---|
| 20 mM histidine buffer, pH 5.0 | 4.97 +/− 0.04 | 5.40 +/− 0.06 | 4.90 +/− 0.14 |
| 32 mM histidine buffer, pH 5.0 | 5.0 +/− 0.04 | 5.20 +/− 0.05 | — |
| 20 mM histidine buffer, pH 7.4 | 7.37 +/− 0.06 | 7.47 +/− 0.05 | 4.81 +/− 0.22 | pH values before UF, after UF and for the end product with readjusted pH to 5.0; 0.5M hydrochloric acid was taken to readjust the pH to pH 5.0 in the end product; mean values of three measurements are presented ± SD.

The adjustment of the solute concentration prior to the UF is calculated based on the following equations 2 and 3.

$$S^+ = \frac{-zP + \sqrt{(zP)^2 + 4\left(\frac{S'}{\rho'}\left(\rho - \frac{PM_P}{1000}\right)\right)^2}}{2} \quad \text{(equation 2)}$$

Equation 2 describes the molar concentration in the retentate of positively charged solutes ($S^+$) being able to pass the membrane. $S^+$ depends on the charge of the protein (z), the molar concentration (P) and the molecular weight ($M_p$) of the protein, as well as on the density of the solution in the retentate ($\rho$) and the permeate ($\rho'$). S' is the theoretical molar concentration of the diffusible solute.

$$S^- = \frac{zP + \sqrt{(zP)^2 + 4\left(\frac{S'}{\rho'}\left(\rho - \frac{PM_P}{1000}\right)\right)^2}}{2} \quad \text{(equation 3)}$$

Equation 3 describes the molar concentration in the retentate of negatively charged solutes ($S^-$) being able to pass the membrane.

For an exemplary immunoglobulin against the amyloid β peptide (anti-Aβ antibody) as reported in WO 2003/070760 or US 2005/0169925 the calculation is made as outlined in the following:

For obtaining a solution with a final immunoglobulin concentration of 200 mg/ml in 20 mM histidine buffer at pH 5.5. The histidine concentration before the concentration step is calculated with equation 2 rearranged to calculate S' as the solute molecule is a positively charged molecule.

The rearranged equation 2 (equation 2') is:

$$S' = \frac{\sqrt{\frac{(2*[S^+]+z*P)^2-(z*P)^2}{4}}}{\rho - \frac{P*M_p}{1000}} *\rho' \quad \text{(equation 2')}$$

The following parameter values were employed:
molecular mass of the immunoglobulin: 150,000 g/mol
density of the permeate: 0.9989 g/ml
molar concentration at end concentration: 0.00133 mol/l
charge of the protein: +9
(determination see Example 13)
starting protein concentration: 15 mg/ml
(determination see Example 4)
target buffer concentration: 0.020 M
density of the protein solution at end of concentration: 1.0551 g/ml
(determination see Example 14)

The values have been entered into equation 2' to result in:

[histidine concentration prior to the concentration] =

$$\frac{((2*0.020+9*0.00133)^2-(9*0.00133)^2)*0.25)^{1/2}}{1.0551-(0.00133*150,000)/1000}*0.9989 \text{ mol/l} =$$

$$0.02955 \text{ mol/l} = 29.6 \text{ mM}$$

Therefore, in order to make the calculation e.g. for a final concentration of 200 mg/ml, the charge of the immunoglobulin to be concentrated according to example 13, the density of the immunoglobulin solution after the concentration according to example 14, and the concentration of the immunoglobulin in the starting immunoglobulin solution according to example 4 have to be determined experimentally.

It is also possible to use literature values for the density of the starting solution according to the following Table 2.

TABLE 2

Density of protein solutions.

| protein concentration [mg/ml] | density of the solution [g/ml] |
|---|---|
| 15 | 1.0105 |
| 28 | 1.0140 |
| 41 | 1.0174 |
| 55 | 1.0211 |
| 68 | 1.0246 |
| 85 | 1.0291 |
| 100 | 1.0331 |
| 112 | 1.0362 |
| 120 | 1.0384 |
| 138 | 1.0431 |
| 185 | 1.0556 |
| 200 | 1.0596 |

The rearranged equation 3 (equation 3') is:

$$S' = \frac{\sqrt{\frac{(2*[S^+]-z*P)^2-(z*P)^2}{4}}}{\rho - \frac{P*M_p}{1000}} *\rho' \quad \text{(equation 3')}$$

In case of an anionic buffer salt (solute) due to the increase of the pH value during the UF process the percentage of buffer salt (solute) in anionic form also increases. Therefore more buffer salt anions will actually be lost than restocked based on the calculation by using the above equations without considering the pH value. Therefore, the theoretical diffusible solute concentration S' has to be corrected by using a factor considering the pH value. The ratio between buffer anion/buffer cation and buffer acid can be calculated for each pH value determined in the retentate by using the Henderson-Hasselbach-Equation. The relative increase at each pH value can be used as the respective correction factor.

The molar solute concentration was approximated by inserting the actual charge value of the immunoglobulin at the pH value in equations 2 and 3, respectively. The overall protein charge was determined by zeta potential measurements (see example 13).

Several possibilities to determine the protein valence depending on the pH value are available. Beside the calculated titration curves based on protein sequence by combining the average $pK_a$-values of all acidic and basic amino acid side chains, the experimental determination based on electrophoretic mobility, like the zeta potential measurement (Faude, A., et al., J. Chromatogr. A 1161 (2007) 29-35; Salinas, B. A., J. Pharm. Sci. 99 (2009) 82-93) or gel- and capillary electrophoresis (Winzor, D. J., et al., Anal. Biochem. 333 (2004) 225-229) is possible. Since the protein valence depends not only upon pH but also on the buffer electrolyte composition of the environment, there is no realistic alternative available to determine the actual charge of the protein.

Two immunoglobulin solutions (see example section for details) were concentrated from 15 mg/ml to 200 mg/ml. One solution used contained 20 mM histidine at pH 5.0 and one solution used contained 20 mM histidine at pH 5.5 before UF. Both immunoglobulin solutions were intended to have 20 mM histidine present at the predefined pH after the concentration process. During UF the displacement of histidine was observed, which was quantitatively corrected by employing equation 2 with a protein charge of +11. At 200 mg/ml immunoglobulin concentration only 10.8 mM histidine remained without restock prior to the UF. It was calculated that 29.6 mM histidine should be present before the UF, to end up with 20 mM histidine after processing at 200 mg/ml protein concentration. Experimental data conducted in a buffer system containing 30.3±0.7 mM histidine at pH 5.5 showed that concentrates at 200 mg/ml exhibit a histidine concentration of 18.6±0.4 mM as predicted. Thus, it was confirmed that by using a higher histidine concentration at the beginning of the UF, calculated by using equation 2', the intended histidine concentration was present after UF up to a target protein concentration of 200 mg/ml.

Moreover, the intended histidine concentration of 46 mM at a protein concentration of 200 mg/ml can be achieved by applying an initially higher histidine concentration of 60 mM before UF as calculated by using equation 2'. In this case a protein charge of +7 was applied.

In case of histidine, the calculated higher solute molarity before starting the UF concentration process resulted in the intended molarities of histidine in the concentrated bulks. Moreover, during and after the UF process the pH value remained almost constant compared to experiments conducted at a lower molarity.

At a protein concentration of 200 mg/ml the pH value was shifted from pH 5.44±0.04 to pH 5.80±0.05, if the histidine concentration was not increased to 29.6 mM histidine before the UF. If the histidine concentration was increased to 29.6 mM, the pH was almost constant, i.e. pH 5.45±0.04 before and pH 5.57 after UF processing.

It has further been found that an adjustment of the pH value is not necessary.

If the pH value is adjusted close to the isoelectric point prior to the tangential flow filtration process the formation of aggregates and particles is induced during the tangential flow filtration process. In contrast thereto the systematic correction of concentration parameters prior to the tangential flow filtration process does not induce the formation of aggregates and/or particles.

Immunoglobulin solutions at a concentration of 20 mg/ml were ultrafiltrated up to 200 mg/ml. Buffer systems based on histidine were used. On the one hand, experiments were conducted in a 29.6 mM histidine buffer pH 5.0. On the other hand UF was performed in a 20 mM histidine buffer pH 7.4. Results were compared to experiments conducted in a buffer system containing 20 mM histidine at pH 5.0 (see FIGS. 6 and 7).

It was observed, that particle formation during of UF was enhanced at pH 7.4. In the course of UF up to $8*10^6$ particles larger than 1 μm were formed and the turbidity increased from 0.1 AU to 1.6 AU. Solutions containing different immunoglobulins ultrafiltrated at a pH value of pH 5.0 were analyzed with respect to particle formation and turbidity. The formation of particles and the turbidity was clearly reduced at this pH value. This can be attributed to the pH value of pH 7.4 which is close to the isoelectric point (IP) of one of the antibodies, which was determined to be about 8 (Nakatsuka, S. and Michaels, A. S., J. Membr. Sci. 69 (1992) 189-211).

Particle measurement, turbidity at 350 nm and SE-HPLC were performed to monitor the induction of aggregate due to the addition of hydrochloric acid. For the readjusted end product an induction of particles larger 1 μm and an increase in turbidity was observed for the solutions concentrated in 20 mM histidine at pH 5.0.

An increase of HMWs from 2.23±0.05% to 2.71% was determined. For the solution containing 29.6 mM histidine at pH 5.0 prior to the UF, the number of particles per ml larger than 1 μm, the turbidity values and the percentage of HMWs remained constant.

After readjusting the pH value from pH 7.4 to pH 5.0 the percentage in HMWs increased from 0.74% to 17.15±0.97%. Concomitantly, the number of particles larger than 1 μm and the turbidity values decreased. Nevertheless, the number of particles and the turbidity values remained much higher compared to the two other processes.

It has been observed, that the addition of a higher molar HCl increases the percentage of dimers as well as of oligomers. This was prevented, by adding a 0.02 M HCl. Concomitantly, the addition of a diluted HCl resulted in a massive dilution of the concentrated protein bulk, ending up with about a third in protein concentration after pH adjustment.

It has also been found that with a change of the pH value prior to the tangential flow filtration process a reduction of the transmembrane flux is associated resulting in a dramatically increased concentration time (see FIG. 8). If a correction of the solute concentration is performed prior to the UF no reduction of the transmembrane flux occurs and the concentration time is unaffected.

The permeate flux was observed to be significantly reduced during processing compared to the experiments conducted at pH 5.0. The process time was more than doubled from 120±2 min. to 300±2 min. when a pH value of pH 7.4 was adjusted before the UF was started. It has been observed, that the addition of histidine prior to the UF step had no influence on the permeate flux.

It has also been found that with the altered buffer composition during the tangential flow filtration process the stability of the concentrated protein is affected.

UF processes are conducted during process and formulation development. Different UF systems, membrane material and operational parameters are applied to concentrate the protein bulk. In order to proof, that the herein presented model is adequately reflecting the experimental values concerning the loss of histidine during UF concentration, different membrane materials, UF systems and operational parameters were tested (see Table 3 and FIG. 5).

TABLE 3

Different set-ups.

| histidine concentration [mM] | pH value | UF membrane material/ pore size [kDa] | UF system | Δp [bar] |
|---|---|---|---|---|
| 20 | 5.0 | RC/30 | stirred cell | 2.0 |
| 20 | 5.0 | RC/30 | cross flow | 0.8 |
| 20 | 5.0 | RC/30 | cross flow | 1.5 |
| 20 | 5.0 | PES/30 | cross flow | 1.5 |

Especially polyethersulfone (PES) is known to adsorb protein to a higher extent than regenerated cellulose (RC), due to enhanced hydrophobicity. Moreover, proteins and solutes can interact with the membrane surface based on charge-charge interactions. As a consequence, the outcome of the solute molarity in the concentrates can be influenced by the choice of the membrane material.

Independent from the applied UF system, membrane material or operational conditions, the experimental data concerning the histidine molarity during UF can be approximated by using the equations as reported before.

In FIG. 10 a graph showing the concentration of histidine to be adjusted prior to the ultrafiltration depending on the intended final protein concentration in order to have a final solution with 20 mM histidine buffer at pH 5.5 exemplified with an anti-Aβ antibody calculated according to the method as reported herein is shown.

The following examples and figures are provided to aid the understanding of the present invention, the true scope of which is set forth in the appended claims. It is understood that modifications can be made in the procedures set forth without departing from the spirit of the invention.

EXAMPLE 1

Material and Methods

Chemicals

Figure 1:
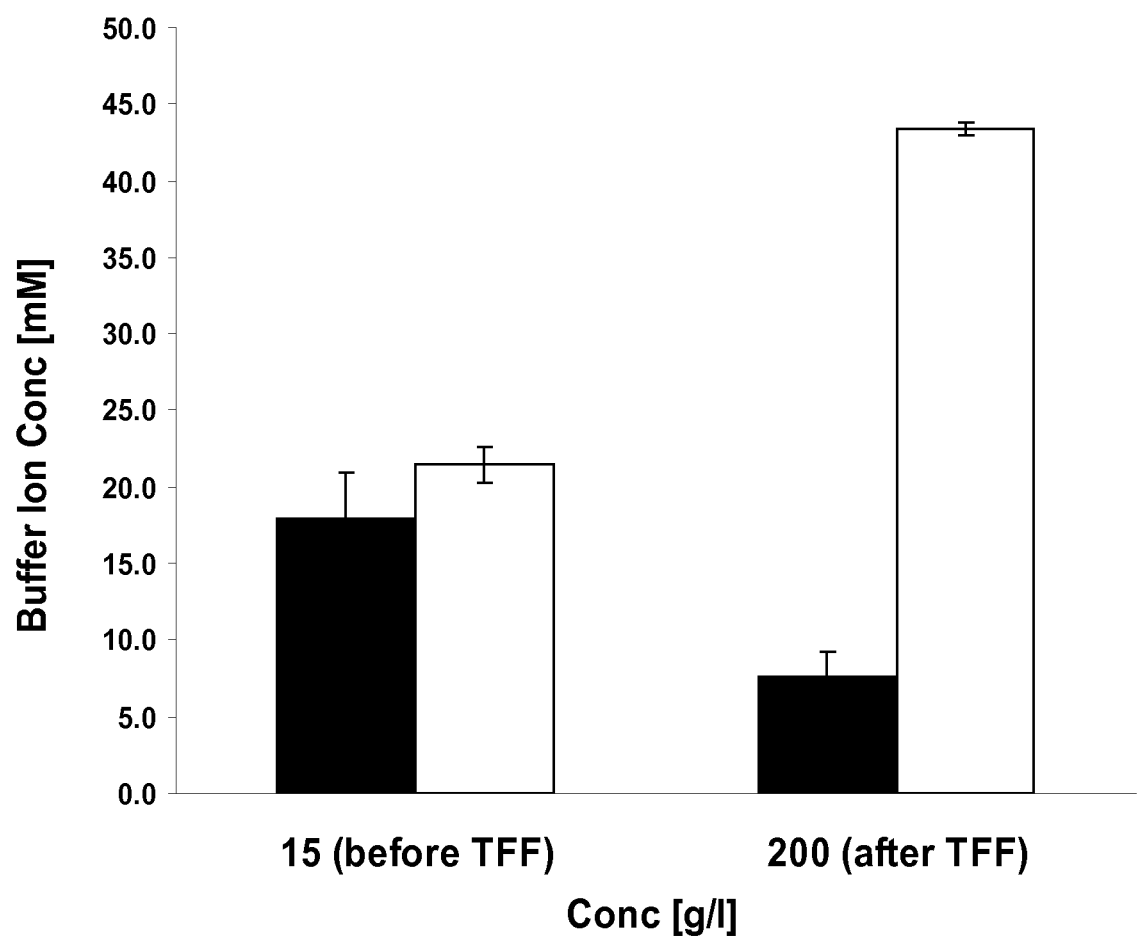
FIG. 1 Buffer ion concentration before and after tangential flow filtration exemplified with a histidine and an acetate buffer exemplified with an anti-Aβ antibody; black=histidine buffer; white=acetate buffer.
Figure 2:
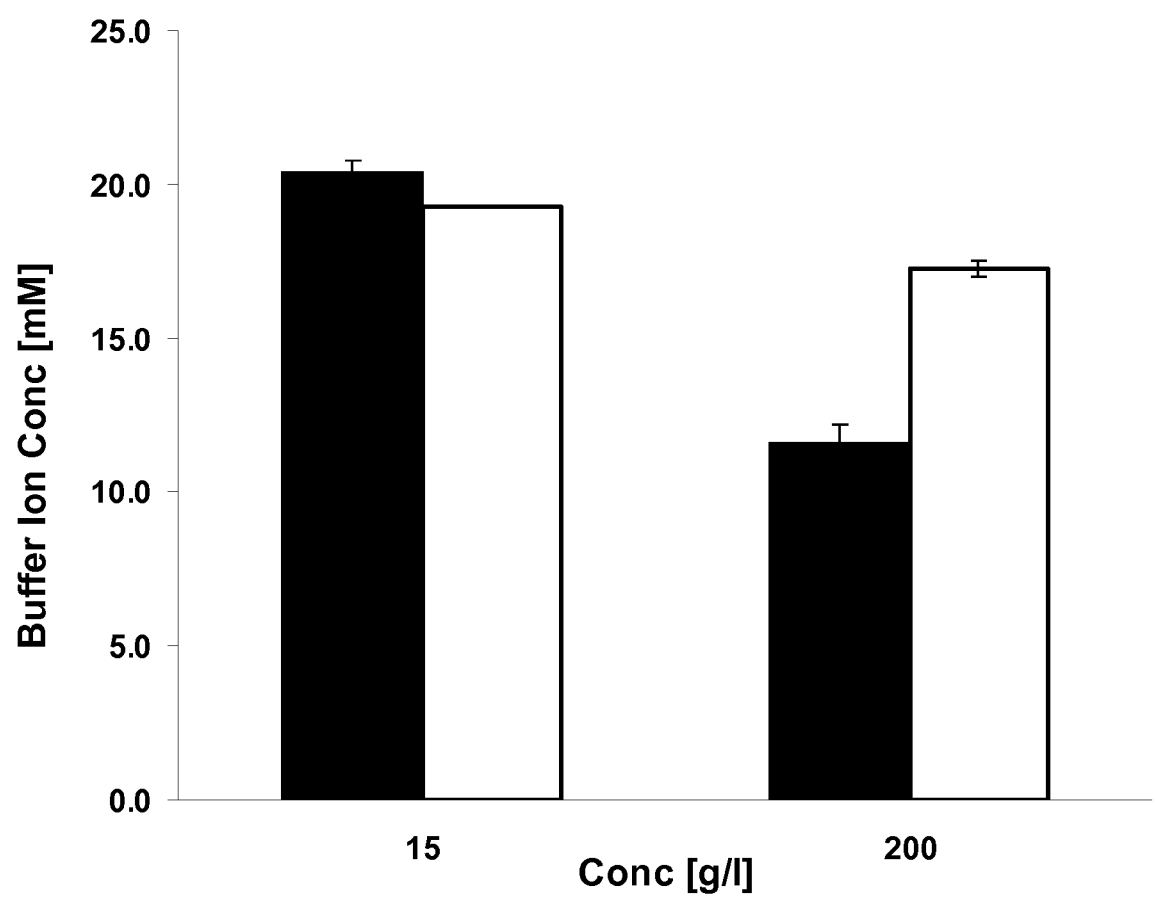
FIG. 2 Buffer ion concentrations before and after tangential flow filtration exemplified with a histidine and an acetate buffer with adjustment of the pH value close to the isoelectric point prior to the tangential flow filtration; black=histidine buffer 20 mM pH 5; white=histidine buffer 20 mM pH 7.5.
Figure 3:
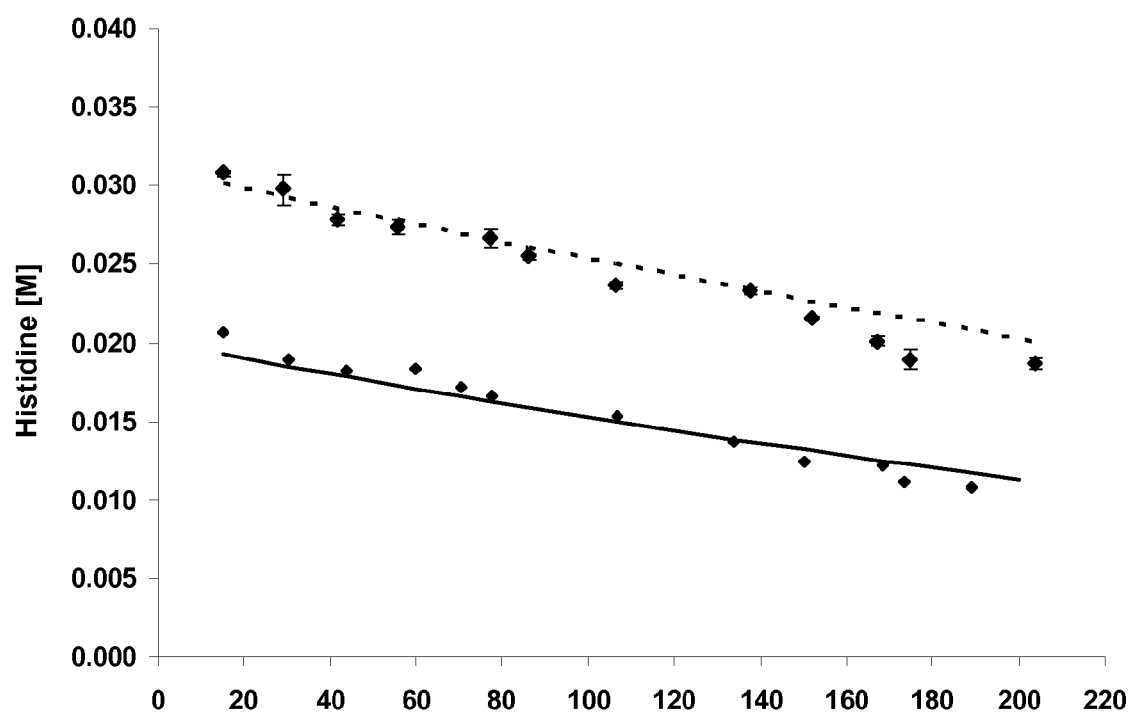
FIG. 3 Course of the buffer ion concentration during tangential flow filtration exemplified with a histidine and an acetate buffer with adjustment of the buffer ion concentration prior to the tangential flow filtration; small diamonds: experimental data of 20 mM histidine buffer, solid line: fit for this data; large diamonds: experimental data of 29.6 mM histidine buffer, dashed lined: fit of this data.
Figure 4:
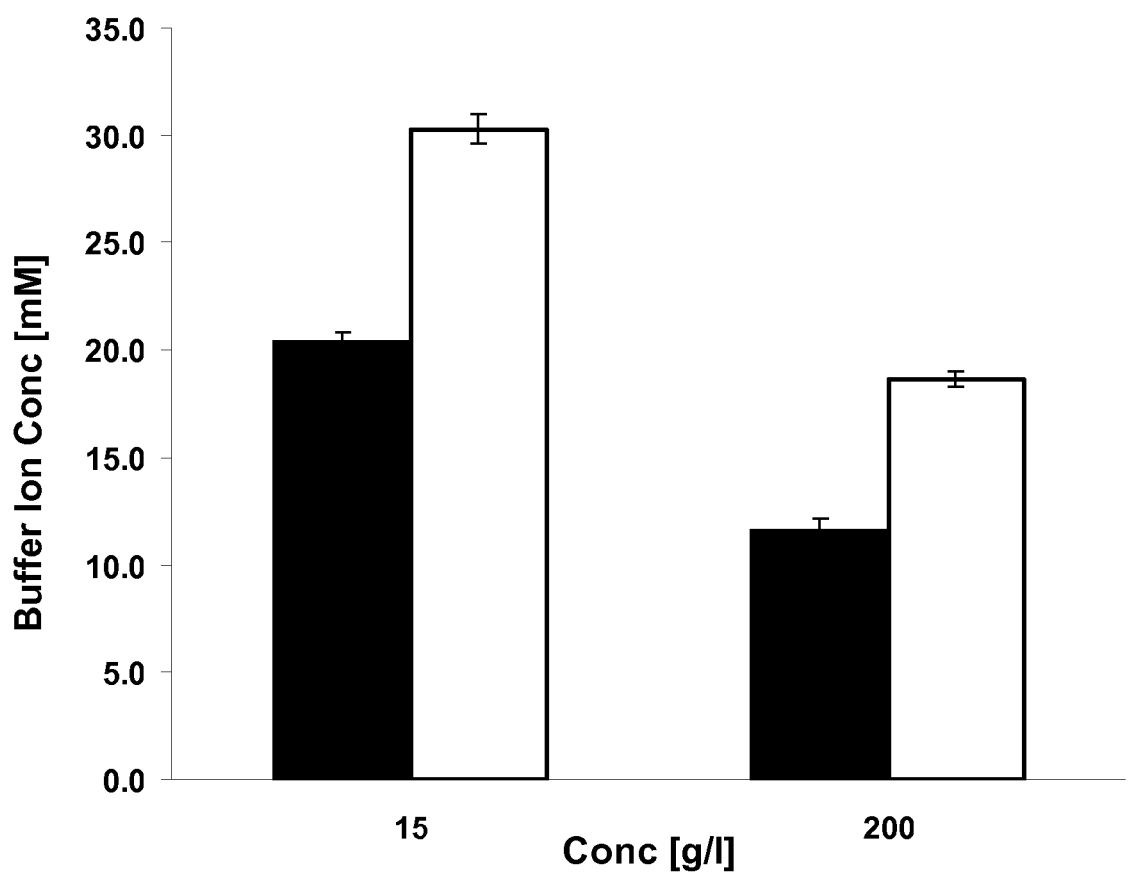
FIG. 4 Buffer ion concentrations before and after tangential flow filtration exemplified with a histidine and an acetate buffer with adjustment of the buffer ion concentration prior to the tangential flow filtration; black=histidine buffer 20 mM; white=histidine buffer 29.6 mM.
Figure 5:
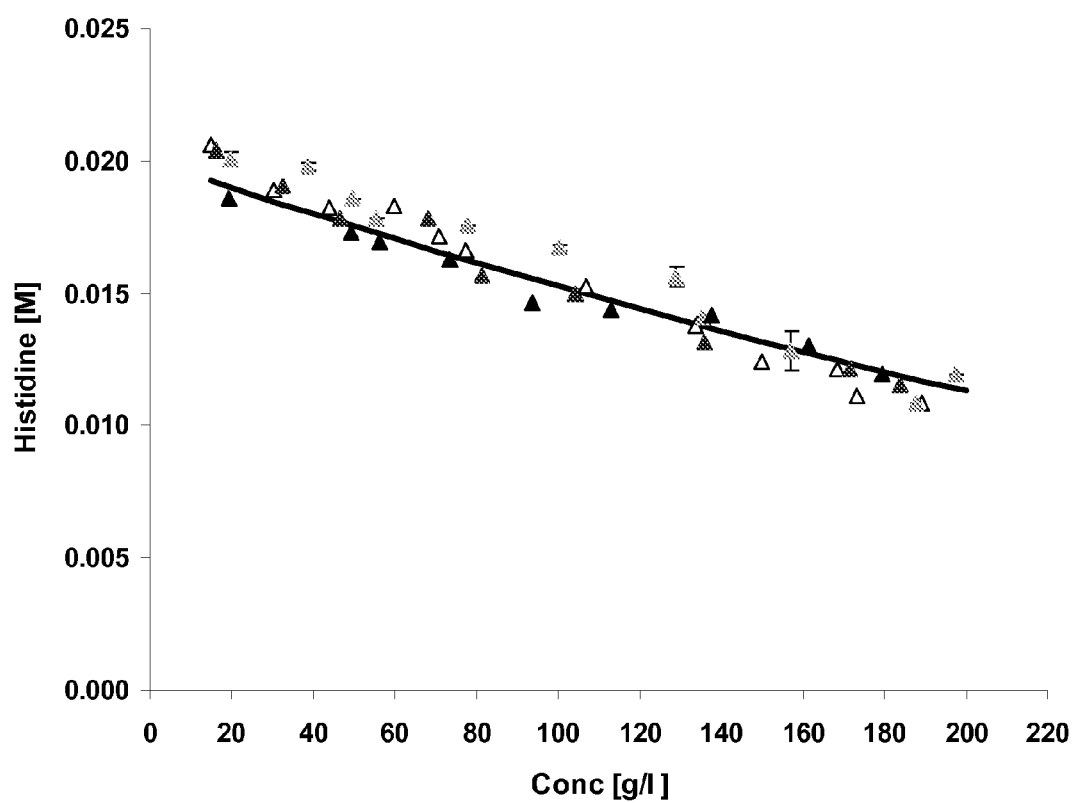
FIG. 5 Change of the buffer ion concentration in a concentration process with different concentration device; solid line: fit; white triangles: Hydrosart™; grey triangles: stirring cell; black small triangles: PESU; black large triangles: ΔP=0.8 bar.
Figure 6:
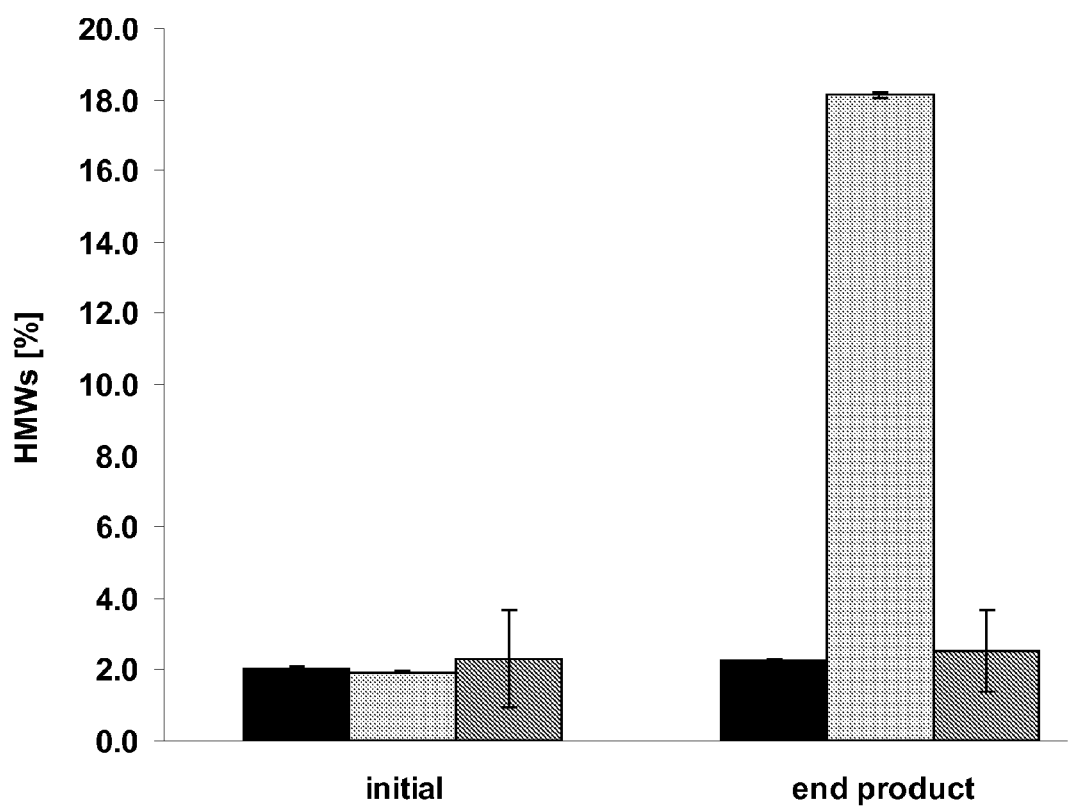
FIG. 6 Induction of high molecular weight compounds during concentration due to pH adjustment; black=concentrated at pH 5.0; light grey=concentrated at pH 7.5; dark grey=concentrated at pH 5 and addition of additional histidine prior to concentration.
Figure 7:
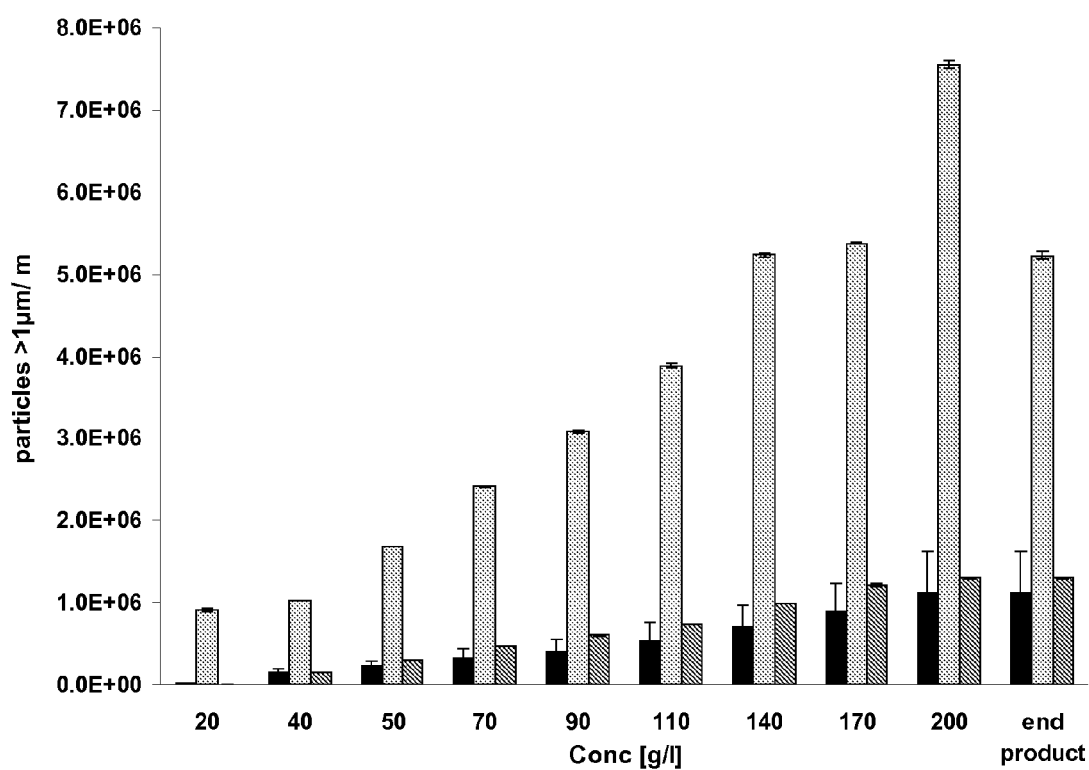
FIG. 7 Induction of particles during concentration due to pH adjustment; black=concentrated at pH 5.0; light grey=concentrated at pH 7.5; dark grey=concentrated at pH 5 and addition of additional histidine prior to concentration.
Figure 8:
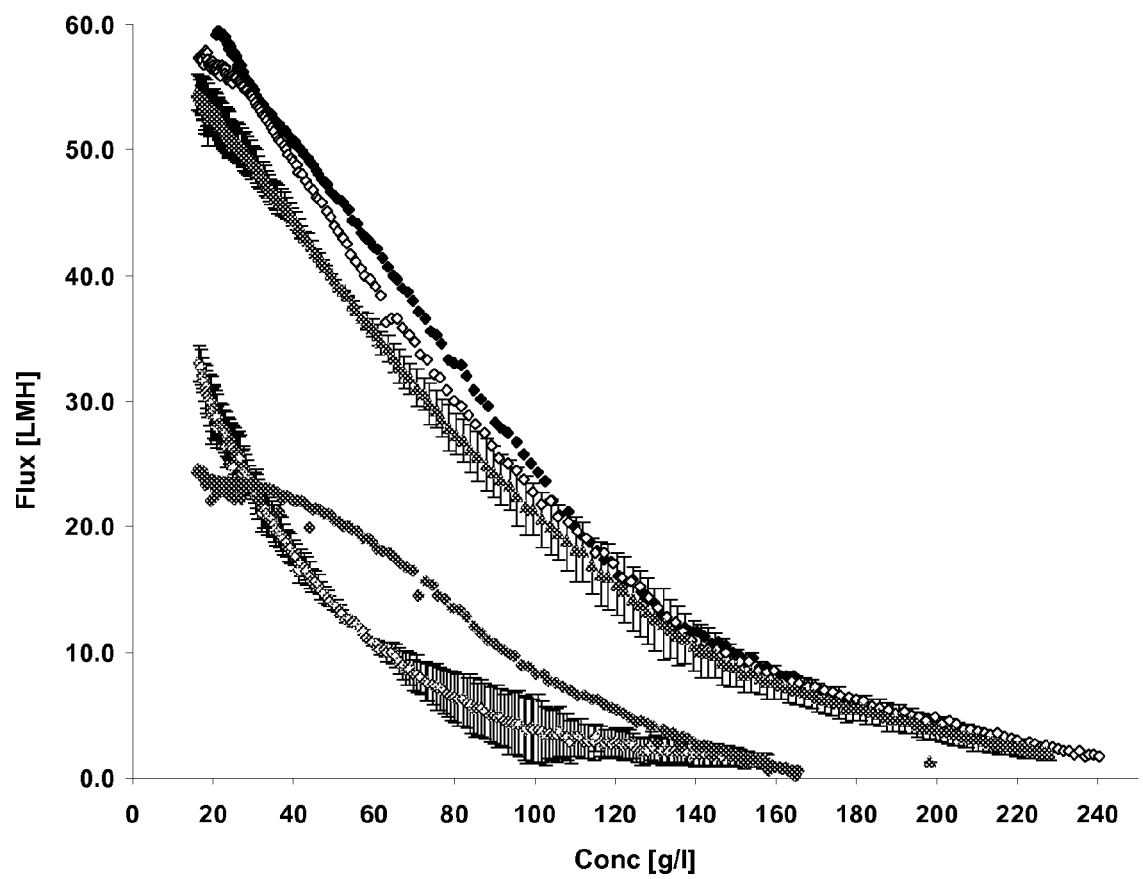
FIG. 8 Dependency of the transmembrane flux on the retentate concentration and on the adjustment method; white small diamond=pH 7.5; grey diamond=pH 5.0 with a P of 0.8 bar; black diamond=pH 5.0 PESU; white large diamond=pH 5.0 Hydrosart™; black triangle=pH 5.0 with addition of histidine prior to concentration.

All chemicals and reagents used were at least analytical grade. Hydrochloric acid and sodium hydroxide were taken from Merck KG (Darmstadt, Germany). L-histidine from Ajinomoto (Raleigh, USA) was used. Acidic acid was taken from Fluka (Steinheim, Germany). Sodium chloride was taken from Merck KG (Darmstadt, Germany).

Antibody

The method as reported herein is exemplified with an immunoglobulin against the amyloid β peptide (anti-Aβ antibody) as reported in WO 2003/070760 or US 2005/0169925. Another exemplary immunoglobulin is an anti-P-Selectin antibody as reported in WO 2005/100402 or US 2005/0226876.

EXAMPLE 2

Sample Preparation

A solution of the immunoglobulin in 20 mM histidine buffer at pH 5.5 and at a concentration of 50 mg/ml was taken for the concentration experiments in histidine buffer. To obtain material containing a higher molarity of histidine, histidine base was added to the protein solution and the pH was adjusted to pH 5.5 by adding 0.1 M hydrochloric acid.

To obtain solutions containing 20 mM and 45 mM acetate buffer pH 5.0, respectively, the 20 mM histidine material was diafiltered against the 10-fold volume of sodium acetate buffer pH 5.0 by using TFF.

A solution of an immunoglobulin in 20 mM histidine buffer at pH 5.0 and a concentration of 20 mg/ml was taken for the experiments in histidine buffer.

Before ultrafiltration (UF) processing the solutions were diluted to 10 mg/ml protein concentration by using the corresponding buffer and filtered through a 0.22 μm membrane cartridge (Sartorius, Göttingen, Germany).

EXAMPLE 3

Tangential Flow Filtration

For the preparation of concentrated immunoglobulin solutions the automated tangential flow filtration (TFF) system ÄKTAcrossflow™ (GE Healthcare, Uppsala, Sweden) was used. The method as reported in WO 2009/010269 was used for all experiments.

In short a retentate flow rate of 240 l/m²/h and a TMP of 1.25 bars were chosen as the condition at the beginning of the UF process for an immunoglobulin concentration of from 5 mg/ml to 25 mg/ml. From 25 mg/ml to 50 mg/ml the TMP was lowered to 0.85 bars. In addition, the retentate flow rate was increased to 450 l/m²/h, bringing the permeate flux from 30 up to 45 l/m²/h. For a concentration range of from 50 mg/ml up to target concentration of 140 mg/ml or more a TMP of 0.85 bars and an increased retentate flow rate of 390 l/m²/h were set.

A Sartocon Slice flat sheet cassette with a Hydrosart™ membrane of regenerated cellulose, with a nominal molecular weight cutoff (NMWC) of 30 kDa and a membrane area of 0.02 m² was used (Sartorius, Göttingen, Germany). The total membrane loading was about 400 g/m² for each experiment. After the concentration the membrane module was cleaned with 1 M sodium hydroxide. The normalized flux rate for water (NWF) was determined after every cleaning cycle and compared to the obtained value before initial use. The cassette was only applied for the next experiments, if the NWF decline in (l/m²/h)/1 bar at 20° C. was below 10% of the initial value to ensure complete cleaning and comparable membrane properties.

EXAMPLE 4

Concentration Determination

Immunoglobulin concentration was determined by using the photometric absorbance at 280 nm and 320 nm after buffer blank subtraction (UV-Vis spectrophotometer Evolution 500, Thermo Fisher Scientific, Waltham, USA). The absorbance at 320 nm was subtracted from the absorbance at 280 nm and this absorbance value was used to calculate the protein content according to the law of Lambert-Beer.

EXAMPLE 5

Conductivity and pH Monitoring

During the TFF process every time the concentration doubled 1 ml was taken from the retentate. The pH was determined by using the Microprocessor pH Meter pH 196 equipped with a pH single-rod measuring cell E50-1.5 from WTW (Weilheim, Germany). The conductivity was determined by using the ProfiLine Konduktumeter LF 197 equipped with a standard conductivity cell TetraCon 325 from WTW (Weilheim, Germany). All samples were tempered in a water bath to 25° C. before measuring pH and conductivity.

EXAMPLE 6

Size Exclusion High Pressure Liquid Chromatography

Size exclusion high pressure liquid chromatography (SE-HPLC) experiments were conducted with a TSK 3000 SWXL column (Tosoh Bioseparation GmbH, Stuttgart, Germany) on a Summit HPLC-system (Dionex, Idstein, Germany). The elution peaks were monitored at 280 nm by the UV diode array detector UVD170U from Dionex (Idstein, Germany). Isocratic chromatography was conducted at room temperature using an aqueous buffer composed of 200 mM potassium phosphate and 250 mM potassium chloride at pH 7.0 and a flow rate of 0.5 ml/min. Each sample contained 100 µg immunoglobulin load per injection. The chromatograms were integrated manually by using the Chromeleon software (Dionex, Idstein, Germany). Percentage of higher molecular weight species (HMWs) including dimers and larger soluble oligomers was determined as relative area (mAU*min.) referred to total area of the two HMW peaks, the monomer peak and the peak of lower molecular weight species (LMWs).

EXAMPLE 7

Histidine Assay

Every time the protein concentration in the retentate doubled the histidine concentration was determined. The samples were diluted to about 100 µM histidine concentration with purified water (Milli-Q, Millipore, Billerica, USA). Afterward, 500 µl diluted sample was mixed with 500 µl perchloric acid (5%) (Fluka, Steinheim, Germany). After 10 min. the sample was centrifuged at 25° C. with 13.000 rpm for 10 min. (miniSpin, Eppendorf, Hamburg, Germany). 100 µl of the supernatant were injected on a MonoS 5/50 GL CEX column (GE Healthcare, Uppsala, Sweden). Chromatographic runs were conducted on a Ultimate 3000 HPLC-system (Dionex, Idstein, Germany) at room temperature using a gradient elution applying two aqueous buffers composed of 50 mM acetate, pH 3.2 (buffer A) and 50 mM acetate, pH 3.2, 1 M sodium chloride (buffer B). A flow-rate of 1.0 ml/min. was applied. Elution was monitored at 210 nm. The chromatograms were integrated manually by using the Chromeleon software (Dionex, Idstein, Germany). To quantify the amount of histidine, the area (mAU*min.) of the defined peak was compared with a standard curve ($r^2$=0.9998).

EXAMPLE 8

Acetate Assay

Every time the protein concentration in the retentate doubled the acetate concentration was determined. The samples were diluted to about 25 mM acetate concentration with purified water (Milli-Q, Millipore, Billerica, USA). Afterwards, 500 µl diluted sample was mixed with 500 µl perchloric acid (5%) (Fluka, Steinheim, Germany). After 10 min. the sample was centrifuged at 25° C. with 13.000 rpm for 10 min. (miniSpin, Eppendorf, Hamburg, Germany). 100 µl of the supernatant were injected on a LiChrosorb RP C18 4/250 column (Merck KG, Darmstadt, Germany). Chromatographic runs were conducted on a Ultimate 3000 HPLC-system (Dionex, Idstein, Germany) at room temperature using a isocratic elution over 15 min. applying a aqueous buffer composed of 6 mM phosphoric acid (Fluka, Steinheim, Germany), pH 2.6 (Kordis-Krapez, M., et al., Food Technol. Biotechnol. 39 (2001) 93-99). After each sample run the column was washed with 3 ml acetonitrile (Merck KG, Darmstadt, Germany) to avoid sample carryover. A flow-rate of 1.0 ml/min. was applied. Elution was monitored at 210 nm. The chromatograms were integrated manually by using the Chromeleon software (Dionex, Idstein, Germany). To quantify the amount of acetate the area (mAU*min) of the defined peak was compared with a standard curve ($r^2$=0.9999).

EXAMPLE 9

Chloride Assay

Every time the protein concentration in the retentate doubled the chloride concentration was determined. The samples were diluted 1:200 with purified water (Milli-Q, Millipore, Billerica, USA). 10 µl of the diluted sample was injected on an IonPac AS11-HC 2/250 column (Merck KG, Darmstadt, Germany). Chromatographic runs were conducted on a ICS 3000 Reagent-Free Ion Chromatography system (Dionex, Idstein, Germany) at room temperature using a gradient elution over 30 min. applying a aqueous solution up to 100 mM sodium hydroxide. A flow-rate of 0.38 ml/min. was applied. Detection was carried out on an ICS 3000 CD conductivity detector. The chromatograms were integrated manually by using the Chromeleon software (Dionex, Idstein, Germany). To quantify the amount of chloride the area (mAU*min) of the defined peak was compared with a standard curve ($r^2$=0.9963).

EXAMPLE 10

Sodium Assay

To quantify the amount of sodium ions, the samples were analyzed with the multi sensor system BioProfile100plus (NOVA Biomedical, Waltham, USA). Sodium ions were quantified at 25° C. after a two point calibration. Samples were diluted 1:1 with purified water (Milli-Q, Millipore, Billerica, USA) before measuring.

EXAMPLE 11

Turbidity Measurement

Turbidity was determined as photometric absorbance of the undiluted concentrates at 350 nm and 550 nm after buffer-blank subtraction, where no intrinsic chromophores of the monoclonal immunoglobulin absorb (UV-Vis spectrophotometer Evolution 500, Thermo Fisher Scientific, Waltham, USA) (Capelle, M. A. H., et al., Eur. J. Pharm. Biopharm. 65 (2007) 131-148). The samples were mixed before measuring. In the presence of suspended particles an increase in UV absorbance at all weave lengths occurs due to scattering effects (Eberlein, G. A., et al., PDA J of Pharmac. Science and Technol. 48 (1994) 224-230).

EXAMPLE 12

Light Obscuration

Light obscuration (LO) was used to monitor the formation of particles in a range of 1-200 µm similar to the method <788> Particulate Matter of Injection in the United States Pharmacopoeia and the European Pharmacopoeia method 2.9.1. (European Directorate for the Quality of Medicine (Ed.), European Pharmacopoeia, Deutscher Apotheker Verlag/Govi-Verlag, Stuttgart/Eschborn, 2001a, 140-141; United States Pharmacopeia Convention (Ed.), United States Pharmacopeia, United States Pharmacopeia Convention, Rockville, Md., 2002, 2046-2051). The particle counter SVSS-C (PAMAS Partikelmess- and Analysesysteme, Rutesheim, Germany) was equipped with a laser diode and a photodiode detector in order to determine the residual photocurrent after particles have passed the course of the beam. As particle sensor the HCB-LD-25/25 was applied. Concentrates of a higher content of particles than 120 000/ml where diluted with buffer to match the specified capacity of the used sensor. Three measurements of a volume of 0.5 ml for each sample were analyzed after an equilibrating flush of 0.3 ml. Results were calculated as mean value of three measurements and referred to a sample volume of 1.0 ml. Before diluting the concentrates the buffer was filtered using Stericup Express plus 0.1 µm filter devices (Millipore, Billerica, USA) and the particle burden was determined as described before.

EXAMPLE 13

Zeta Potential Measurement

Figure 9:
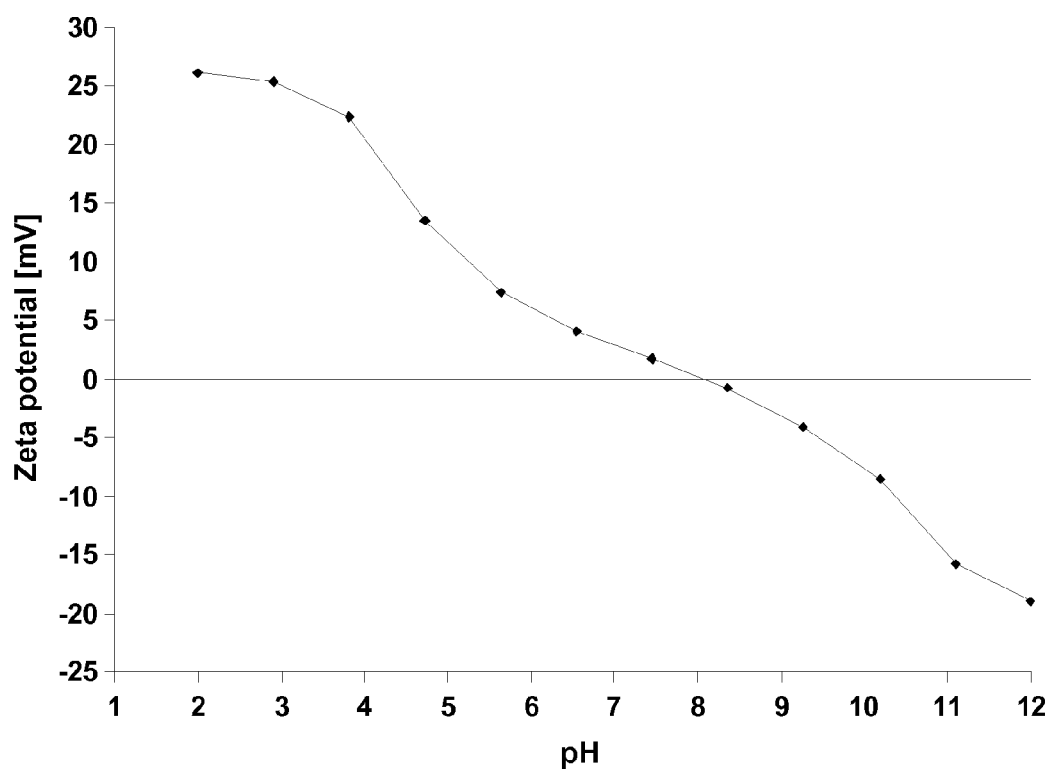
FIG. 9 Zeta potential determined according to Example 13 for an anti-IL-1R antibody.
Figure 10:
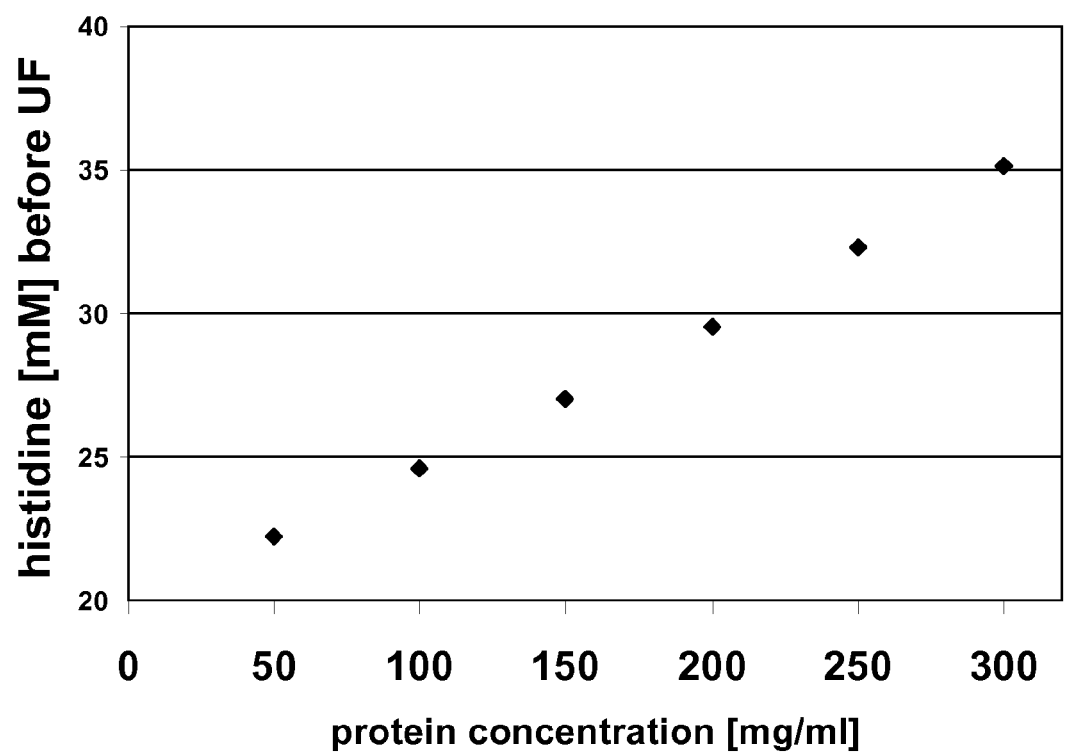
FIG. 10 Graph showing the concentration of histidine to be adjusted prior to the ultrafiltration depending on the intended final protein concentration in order to have a final solution with 20 mM histidine buffer at pH 5.5 exemplified with an anti-Aβ antibody.

To determine the charge of the protein at different pH values, electrophoretic mobility of the protein was determined by performing Laser-Doppler-Velocimetry using the Malvern Zetasizer Nano S (Malvern Instruments, Worcestershire, UK). The zeta potential ζ was calculated from the Henry's equation with assumption of uniform charge distribution by using the Malvern DTS software (Version 5.0, Malvern Instruments, Worcestershire, UK):

$$\mu_e = \frac{2\varepsilon k\zeta}{3\eta}$$ (equation 4)

Where $\mu_e$ is the electrophoretic mobility, $\varepsilon$ is the dielectric constant of the solution, $k_s$ is the model based constant with a value of 1.5 for a salt concentrations higher than 1 mM, η is the viscosity of the solution and ζ is the zeta potential. For sample preparation the 5 mg/ml mAb solutions were dialyzed into 50 mM acetate buffer pH 5.0 and titrated to a pH of 2.0 afterwards by using 0.2 M hydrochloric acid. The samples were titrated with a 0.2 M sodium hydroxide solution from pH 2 to pH 12 by applying the titrator MPT2 (Malvern Instruments, Worcestershire, UK). The zeta potential was determined in 15 steps between pH 2 and 12 in a temperature controlled folded capillary cell (Malvern Instruments, Worcestershire, UK) at 25° C. Each measurement was repeated threefold and mean values±SD are reported. See FIG. 9 for an exemplary zeta potential determination of an anti-IL-1R antibody.

EXAMPLE 14

Determination of Protein Solution Density

The density ρ of the protein solutions was determined at every protein concentration step. A pycnometer (Schott, Mainz, Germany) with a volume of 2.076 ml was filled with the sample solution previously tempered to 20° C. The mass of the unfilled and filled pycnometer was determined by using an analytical balance (MC 210 S, Sartorius, Göttingen, Germany). The density was calculated according to the common equation $\rho$ =m/V.

The invention claimed is:
1. A method for concentrating an immunoglobulin solution comprising the following steps:
   a) providing an immunoglobulin solution with a pH value, with a first immunoglobulin protein concentration, and with a first concentration $S^+$ or $S^-$ of a buffer substance,
   b) adjusting said first concentration of said buffer substance to a second concentration S' and maintaining said pH value, whereby said second concentration S' is calculated with equation 2 if said buffer substance is a cation/neutral pair or with equation 3 if said buffer substance is a neutral/anion pair,
   c) concentrating the solution of b) with a tangential flow filtration to a second immunoglobulin protein concentration, wherein equation 2 is $$S^+ = \frac{-zP + \sqrt{(zP)^2 + 4\left(\frac{S'}{\rho'}\left(\rho - \frac{PM_P}{1000}\right)\right)^2}}{2}$$

and equation 3 is $$S^- = \frac{zP + \sqrt{(zP)^2 + 4\left(\frac{S'}{\rho'}\left(\rho - \frac{PM_P}{1000}\right)\right)^2}}{2}$$

with the molar concentration in the retentate of positively/negatively charged solutes ($S^+$/$S^-$), the charge of the protein (z), the molar concentration (P) and the molecular weight ($M_P$) of the protein, the density of the solution in the retentate ($\rho$) and the permeate ($\rho'$), and the theoretical molar concentration of the diffusible solute (S').

2. The method of claim 1, wherein said buffer substance is histidine and that said second concentration is calculated with equation 2.

3. The method of claim 1, wherein said first concentration is approximately 20 mM.

4. The method of claim 3, wherein said second concentration is of from 24 mM to 37 mM.

5. The method of claim 1, wherein wherein said first concentration is approximately 46 mM.

6. The method of claim 5, wherein said second concentration is of from 52 mM to 72 mM.

7. The method of claim 1, wherein said buffer substance is acetate and that said concentration is calculated with equation 3.

8. The method of claim 7, wherein said first concentration is 20 mM.

9. The method of claim 8, wherein said second concentration is of from 8 to 19 mM.

10. The method of claim 7, wherein said first concentration is 45 mM.

11. The method of claim 10, wherein said second concentration is of from 41 mM to 48 mM.

12. The method of claim 1, wherein the immunoglobulin is an anti-P selectin antibody or an anti-Aβ antibody.

13. A method for producing an immunoglobulin comprising
   a) cultivating a cell comprising a nucleic acid encoding said immunoglobulin,
   b) recovering said immunoglobulin from the cultivation medium or the cell of step a)
   c) purifying said immunoglobulin,
   d) concentrating said immunoglobulin with the method of claim 1 and thereby producing an immunoglobulin.

* * * * *